US010292810B1

(12) United States Patent
Haddock et al.

(10) Patent No.: US 10,292,810 B1
(45) Date of Patent: May 21, 2019

(54) INTRAOCULAR LENS WITH DYNAMIC PINHOLE

(71) Applicant: VERILY LIFE SCIENCES LLC, Mountain View, CA (US)

(72) Inventors: Joshua N. Haddock, Mountain View, CA (US); Dimitri T. Azar, Chicago, IL (US)

(73) Assignee: Verily Life Sciences LLC, South San Francisco, CA (US)

( * ) Notice: Subject to any disclaimer, the term of this patent is extended or adjusted under 35 U.S.C. 154(b) by 270 days.

(21) Appl. No.: 15/055,190

(22) Filed: Feb. 26, 2016

(51) Int. Cl.
*A61F 2/16* (2006.01)

(52) U.S. Cl.
CPC .......... *A61F 2/1624* (2013.01); *A61F 2/1613* (2013.01); *A61F 2/1659* (2013.01); *A61F 2002/1683* (2013.01); *A61F 2002/1696* (2015.04); *A61F 2250/0053* (2013.01)

(58) Field of Classification Search
CPC .... A61F 2/1659; A61F 2/1624; A61F 2/1613; A61F 2002/1696; A61F 2250/0053; A61F 2250/0091
See application file for complete search history.

(56) References Cited

U.S. PATENT DOCUMENTS

| 7,452,067 | B2 | 11/2008 | Gross |
| 7,646,549 | B2 | 1/2010 | Zalevsky |
| 8,197,539 | B2 | 6/2012 | Nasiatka et al. |
| 2009/0204207 | A1* | 8/2009 | Blum ....................... G02C 7/08 623/4.1 |
| 2013/0268071 | A1* | 10/2013 | Vilupuru ................ A61B 3/102 623/6.17 |
| 2014/0002789 | A1 | 1/2014 | Pugh et al. |
| 2014/0168602 | A1 | 6/2014 | Weeber |

* cited by examiner

*Primary Examiner* — William H Matthews
(74) *Attorney, Agent, or Firm* — Christensen O'Connor Johnson Kindness PLLC (57) ABSTRACT

Embodiments of an intraocular lens are described. The intraocular lens includes a lens having a center and having positive or negative optical power and a pinhole mask formed on the lens. The pinhole mask includes one or more annular sections whose centers substantially coincide with the center of the lens, each of the one or more concentric annular sections having variable opacity, and a central section that is permanently transparent, the radius of the central section being adapted to allow the central section to act as a pinhole when the one or more concentric annular sections are made opaque.

28 Claims, 9 Drawing Sheets

INTRAOCULAR LENS WITH DYNAMIC PINHOLE

TECHNICAL FIELD

The disclosed embodiments relate generally to intraocular lenses and in particular, but not exclusively, to an intraocular lens with a dynamic pinhole.

BACKGROUND

Intraocular lenses (IOLs) are used to treat cataracts. IOLs are surgically implanted in an eye by cutting the eye open and inserting the IOL. Typical IOLs include a small lens with side struts called haptics that hold the lens in place inside the eye.

IOL insertion, also known as lens replacement surgery, is a common ophthalmological procedure. It is frequently completed in less than 30 minutes, is performed with local anesthesia, and has a relatively short recovery time (approximately 2-3 weeks). But one major disadvantage associated with lens replacement surgery, and the conventional IOLs used, is that conventional IOLs are typically only focused for long distance sight. Because IOLs are somewhat more rigid than the eye's natural lens, patients who undergo standard IOL implantation largely lose their ability to accommodate (change the focal length of their eye(s) from near to far) because the ciliary muscle in the eye can no longer change the shape of the lens.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified. Drawings are not to scale unless specifically indicated.

DETAILED DESCRIPTION OF THE ILLUSTRATED EMBODIMENTS

Embodiments are described of an apparatus, system and method for intraocular lenses including a dynamic pinhole. Specific details are described to provide an understanding of the embodiments, but one skilled in the relevant art will recognize that the invention can be practiced without one or more of the described details or with other methods, components, materials, etc. In some instances well-known structures, materials, or operations are not shown or described in detail but are nonetheless encompassed within the scope of the invention.

Reference throughout this description to "one embodiment" or "an embodiment" means that a described feature, structure, or characteristic can be included in at least one described embodiment. Appearances of "in one embodiment" or "in an embodiment" therefore do not necessarily all refer to the same embodiment. Furthermore, the described features, structures, or characteristics can be combined in any suitable manner in one or more embodiments.

One way to overcome this challenge of conventional IOLs is to use a dynamic optic with a very large depth of field—i.e., one that can provide reasonably good corrected vision over a large range of object distances. Reducing the physical size of the aperture of an imaging system will increase its depth of field; this is the principle that governs the operation of a pinhole camera. A potential drawback of this approach is that as the size of the optical aperture is reduced the amount of transmitted light will be reduced as well. Small optical apertures can result in dim, low contrast images. A way to mitigate this effect in a dynamic IOL device is to use a dynamic aperture or pinhole that can be activated when only or mostly when the wearer is using near vision—or, put differently, anything other than distance vision. At all other times the aperture would be off and not limit the transmission of light through the eye.

Figure 1:
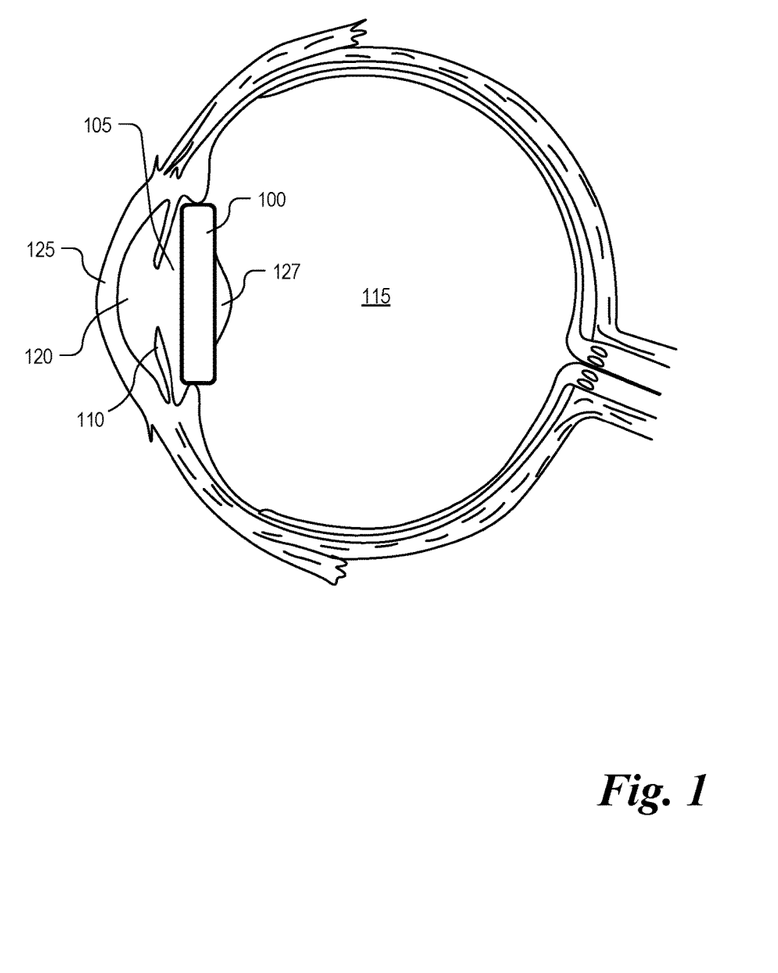
FIG. 1 is a cross sectional illustration of a human eye including an embodiment of an intraocular lens system.

FIG. 1 is a cross sectional illustration of an eye 115 including an embodiment of an intraocular lens (IOL) system 100 with a dynamic pinhole. IOL system 100 is one possible implementation of an IOL system with a dynamic pinhole, such as the ones whose description follows. In the depicted embodiment, IOL system 100 has been inserted into the eye to replace the eye's natural lens. IOL system 100 is illustrated implanted within the posterior chamber 105, where it is held in the capsular bag 127 behind iris 110, but in other embodiments IOL system 100 can be implanted into other locations in the eye, such as anterior chamber 120 between iris 110 and cornea 125.

In operation, IOL system 100 can provide optical accommodation by employing a dynamic pinhole to provide a greater depth of field, thus allowing the eye to more easily focus on different focal distances, especially at near focal distances. A pinhole mask that controls the presence, size, or both, of a pinhole on the lens can be disposed in/on a lens or can include an integrated or physically distinct lens controller system. In one embodiment, IOL system 100 includes a lens with a liquid crystal pinhole mask that utilizes the presence, size, or both, of a pinhole for dynamic accommodation control. In one embodiment, a microelectronic control system can be disposed along the perimeter of the lens to control the pinhole mask (see, e.g., FIGS. 3A-3B).

Figure 2:
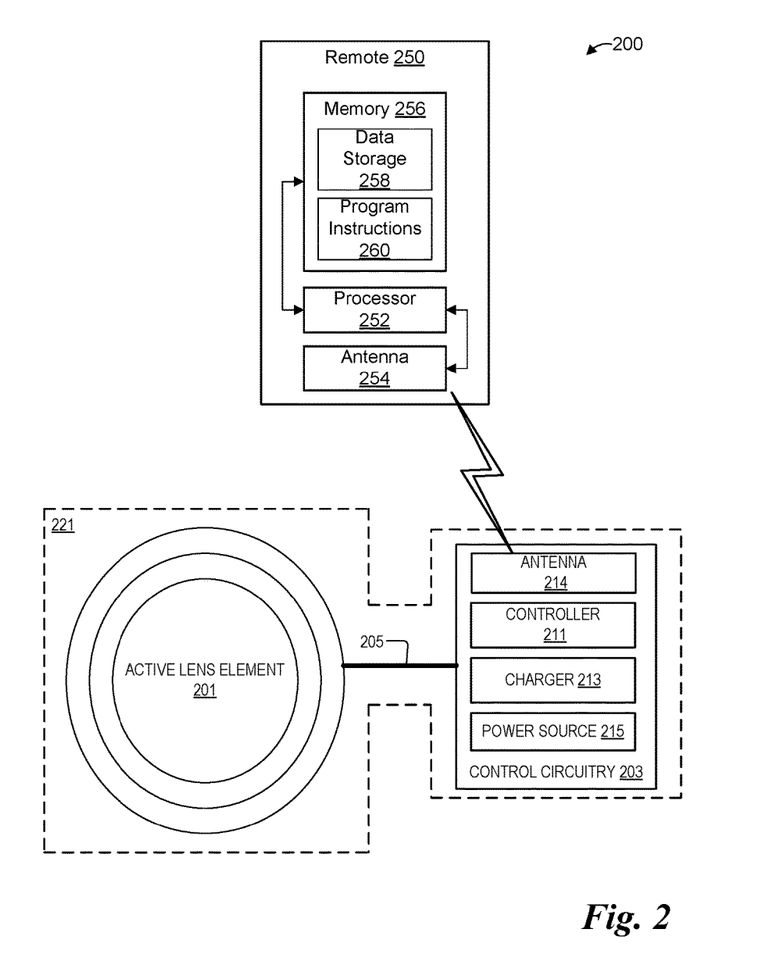
FIG. 2 is a functional block diagram of an embodiment of an active intraocular lens system.

FIG. 2 illustrates, in functional block diagram form, an embodiment of an active accommodating intraocular lens (IOL) system 200. IOL system 200 includes active lens element 201, control circuitry 203, encapsulation layer 221, and conductive tether 205. The illustrated embodiment of control circuitry 203 includes controller 211, charger 213, power source 215, and antenna 214. Active lens element 201 provides a dynamic pinhole for active accommodation; "dynamic" in this context means that the pinhole can appear and disappear and, in some embodiments, can change size when it appears.

Active lens element 201 is coupled to control circuitry 203, which controls active lens element 201 during the accommodation process. In the illustrated embodiment control circuitry 203 is separate from active lens element 201 and is coupled via a conductive tether 205, but in other embodiments control circuitry 203 can be physically included in/on active lens element 201 or immediately adjacent thereto (see, e.g., FIGS. 3A-3B). Control circuitry 203 can be disposed along the periphery of active lens element 201 to avoid interference with optical accommodation devices that can be disposed in the center of active lens element 201. In one embodiment active lens element 201 can include a pinhole mask in the center of active lens element 201 based on liquid crystal devices (see, e.g., FIGS. 6-7), but in other embodiments the pinhole mask can be based on fluidic devices, electrowetting devices, microelectromechanical (MEMS) devices, electrochromic device, or the like in the center of active lens element 201.

Control circuitry 203 can contain a variety of sub-elements including controller 211. In the illustrated embodiment controller 211 is coupled to control active lens element 201. In one embodiment control logic in controller 211 is implemented as hardware logic (e.g. ASIC, FPCA, etc.) and/or firmware instructions, but in other embodiments control logic in controller 211 can be implemented in software that can be altered after IOL system 200 has been inserted into the eye, for instance wirelessly using remote 250. In still other embodiments the control logic can be a combination of hardware and software.

Power source 215 is coupled to provide power to controller 211, active lens element 201, and antenna 214. In one embodiment power source 215 includes a battery such as a lithium ion battery or the like, but in other embodiments power source 215 can include other power sources such as a capacitor. Power source 215 is coupled to charger 213 which provides charge to power source 215. In one embodiment charger 213 can contain a photovoltaic device. In another embodiment, charger 213 can include an inductive charging system that receives electromagnetic radiation and converts the electromagnetic radiation into charge via induction. Once active accommodating IOL system 200 has been successfully inserted into the eye, charger 213 can receive electromagnetic radiation from an inductive charging apparatus.

The user of the active accommodating IOL system 200 can be notified of a low-power situation by a display in active lens element 201, prompting the user to use the charging apparatus. Additionally, IOL system 200 can communicate with the charging apparatus via a variety of electromagnetic transmission technologies including backscatter radio-frequency identification, or the like. In this manner, software installed on the active accommodating IOL system 200 can be updated.

In the illustrated embodiment, active accommodating IOL system 200 is encased in encapsulation layer 221. Encapsulation layer 221 is disposed on a surface of active accommodating IOL system 200. Encapsulation layer 221 can include a single layer or many layers of encapsulant that is spray coated, dip coated, or the like onto active accommodating IOL system 200. Furthermore, encapsulation layer 221 can cover all of, or only some of, active accommodating IOL system 200. In one embodiment, encapsulation layer 221 can include biocompatible polymer materials such as silicone, polyethylene, polypropylene, polymethymethacrylate, polyethyleneoxide, polyvinylalcohol, or otherwise. Encapsulation layer 221 can also be a physical enclosure made of metal, glass, ceramic, etc., or a combination thereof.

In some embodiments it can advantageous for a user to be able to operate active lens element 201 manually, for instance using a wireless remote 250 that can communicate with controller 211. Remote 250 can include a processor 252 coupled to an antenna 254 and a memory 256. Memory 256 can include data storage 258 and program instructions 260. Processor 256, together with data storage 258 and program instructions 260, can be used to provide instructions to controller 211 wirelessly via antenna 254 on remote 250 and antenna 214 in control circuitry 203, for instance via backscatter communication.

Figure 3A:
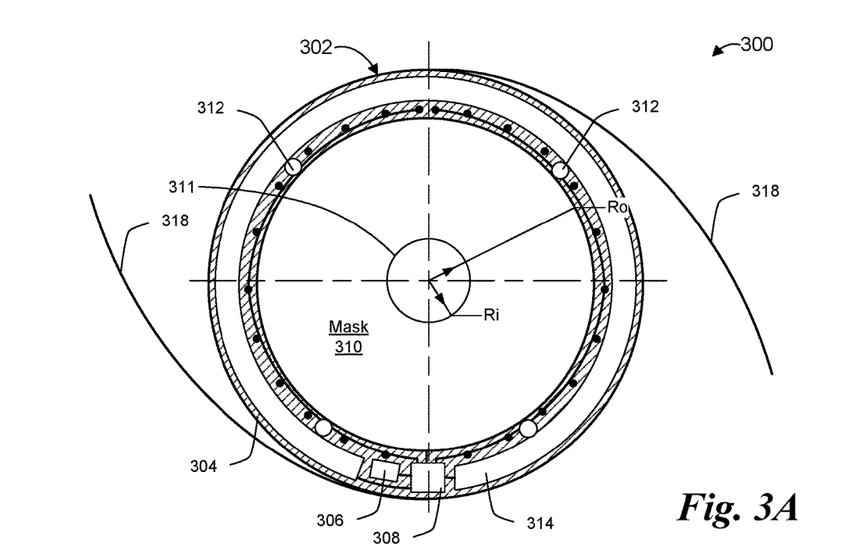
FIGS. 3A-3B are plan views of an embodiment of an intraocular lens including a pinhole mask.
Figure 3B:
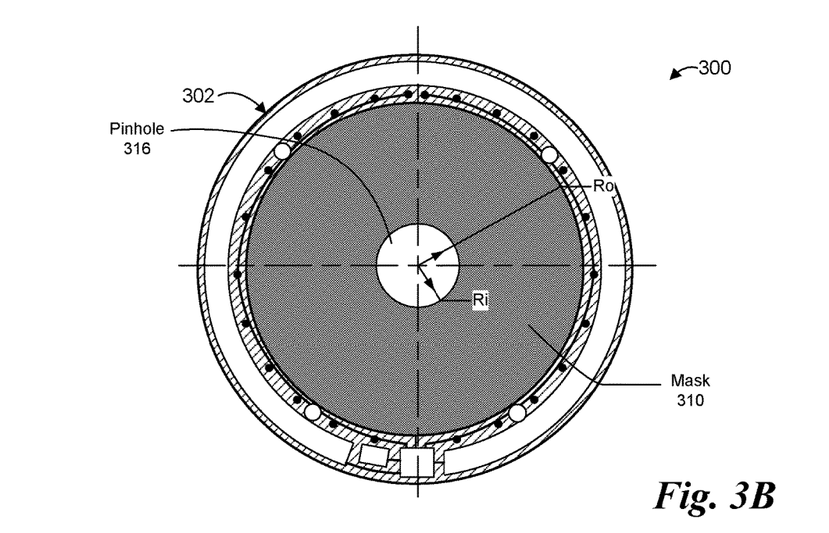

FIGS. 3A-3B illustrate an embodiment of an active intraocular lens 300. Intraocular lens 300 includes a lens 302, a ring substrate 304, a power supply 306, a controller 308, a dynamic variable-opacity pinhole mask 310, a sensor system 312, and an antenna 314. Haptics 318 extend from the edges of lens 302 to help keep it properly positioned in the eye.

Ring substrate 304 is formed on lens 302. Ring substrate 304 can be embedded so that it is positioned along the outer periphery of lens 302, away from the central region where pinhole mask 310 is positioned. In the illustrated embodiment ring substrate 304 encircles pinhole mask 310 but does not interfere with vision because it is positioned away from the central region where incident light is transmitted to the light-sensing portions of the eye and, in any event, is too close to the eye to be in focus. In some embodiments ring substrate 304 can optionally be formed of a transparent material to further reduce effects on visual perception. Ring substrate 304 can be shaped as a flat, circular ring or annulus (e.g., a disk with a centered hole). The flat surface of ring substrate 304 (e.g., along the radial width of the annulus) is a platform for mounting electronics and for patterning conductive materials to form electrodes, antenna(e), and/or interconnections.

In some embodiments sensor system 312 can include one or more discrete sensors peripherally distributed around ring substrate 304. Sensor system 312 is distributed about IOL 300 to sense whether the wearer is using distance vision or near vision. In the illustrated embodiment, sensor system 312 is formed by a series of parallel-coupled individual sensors, but other implementations can be used. Use of a pinhole to increase depth of field is most advantageous with near vision, so by monitoring feedback signals from sensor system 312 the need for a pinhole, and its size if needed, can be determined and the pinhole mask activated accordingly. In various embodiments the individual sensors in sensor system 312 could be strain gauges that measure the load applied to lens 302 by the ciliary muscles, electrical gauges that measure electrical activity of the ciliary muscle, or optical and other sensors that can measure the position and convergence of the wearer's eyes. In still other embodiments a user could activate the pinhole mask manually using a remote control that can communicate with IOL 300 via antenna 314 (see, e.g., FIG. 2).

Dynamic pinhole mask 310 is centrally positioned on lens 302 to affect the size of the vision aperture, "dynamic" in this context meaning that the pinhole mask can make the pinhole appear and disappear and, in some embodiments, can change in size when it appears. In one embodiment pinhole mask 310 is circular with radius Ro, such that it covers a lens 302, but has a central area 311 in which it the opacity is low (i.e., its transmission is high) and cannot change, or at least not change significantly (see, e.g., FIGS. 8-9). In this embodiment, because the opacity of central area 311 changes little or not at all, the central region is permanently transparent (i.e., in a high-transmission state) and never becomes opaque when the rest of the mask becomes opaque. Central region 311 forms pinhole 316 when pinhole mask 310 is activated (see FIG. 3B)

In another embodiment pinhole mask 310 is annular, so that it covers all of lens 302 except central area 311. In an embodiment where pinhole mask 310 is annular it has an outer radius Ro, an inner radius Ri, and a width W=Ro−Ri. Because pinhole mask 310 is annular it does not cover a central region 311 of the lens, meaning that the central region is permanently transparent and never becomes opaque when the mask becomes opaque. Central region 311 forms pinhole 316 when pinhole mask 310 is activated (see FIG. 3B). In various embodiments, pinhole mask 310 includes an element that changes its opacity (or, put differently, changes it transmission) under the influence of controller 308 (see, e.g., FIGS. 6-7).

A sealing or insulating region can be disposed between pinhole mask 310 and ring substrate 304 to seal the pinhole mask electrically isolate at least some circuitry of ring substrate 304. Pinhole mask 310 can be implemented using a variety of different optoelectronic elements as shown, for instance, in FIGS. 6-7, that use other sealing structures such as dams or crimped edges.

In some embodiments sensor system 312 can include one or more discrete sensors peripherally distributed around ring substrate 304. Sensor system 312 is distributed about IOL 300 to sense whether the wearer is using distance vision or near vision. In the illustrated embodiment, sensor system 312 is formed by a series of parallel-coupled individual sensors, but other implementations can be used. Use of a pinhole to increase depth of field is most advantageous with near vision, so by monitoring feedback signals from sensor system 312 the need for a pinhole, and its size if needed, can be determined and the pinhole mask activated accordingly. In various embodiments the individual sensors in sensor system 312 could be strain gauges that measure the load applied to lens 302 by the ciliary muscles, electrical gauges that measure electrical activity of the ciliary muscle, or optical and other sensors that can measure the position and convergence of the wearer's eyes. In still other embodiments a user could activate the pinhole mask manually using a remote control that can communicate with IOL 300 via antenna 314 (see, e.g., FIG. 2).

FIG. 3B illustrates IOL 300 with pinhole mask 310 activated. When the pinhole mask is activated by controller 308 its opacity increases, blocking incident light from traveling through the mask. In an embodiment where pinhole mask 310 is circular the whole mask except central area 311 increases its opacity, but in an embodiment where pinhole mask 310 is annular the whole mask increases its opacity. Since substantially less light can travel through the activated mask but the mask does not obscure central area 311, the activated mask effectively creates a pinhole 316 in the center of the lens at central area 311. In an embodiment of IOL 300 lens 302 has an outer diameter of 5-6 mm and central area 311, and thus pinhole 316, has a diameter (i.e., a pinhole diameter) of 1-3 mm.

In various embodiments pinhole mask 310 can vary its transmission between 0% and 100% of the incident light. In one embodiment, when the transmission of pinhole mask 310 is high (i.e., its opacity is low) it can transmit 90% or more of the incident light, but in other embodiments when the transmission of pinhole mask 310 is high it can transmit between 50% of the incident light and 90% of the incident light. In one embodiment, when the transmission of pinhole mask 310 is low (i.e., its opacity is high) it can transmit less than 10% of the incident light, but in other embodiments when the transmission of pinhole mask 310 is low it can transmit between 10% and 50% of the incident light.

FIGS. 4A-4E illustrate another embodiment of a dynamic pinhole mask 400 that can be used in an intraocular lens system such as intraocular lens 300. Like pinhole mask 310, pinhole mask 400 is formed on lens 402. But rather than being a single annulus like pinhole mask 310, pinhole mask 400 includes multiple nested annuluses A1-A4. A central area 404 is not covered by any of annuluses A1-A4 and remains permanently transparent. The illustrated embodiment includes four annuluses A1-A4, but other embodiments of pinhole mask 400 can have a different number of annuluses, typically two or greater.

Annuluses A1-A4 are concentric, meaning that they share the same center, and that center substantially coincides with the center of lens 402 and central area 404. Each annulus has an inner radius, an outer radius, and a width equal to the difference between its inner and outer radius. Outermost annulus A4, for instance, has outer radius R4 and inner radius R3, giving it a width W4 equal to R4-R3. The other annuluses are similar: innermost annulus A1, for instance, has outer radius R1, inner radius R0, and width W1=R1−R0. In the illustrated embodiment all annuluses A1-A4 have substantially equal widths W—in other words, W1=W2=W3=W4. But in other embodiments (see e.g., FIGS. 5A-5E) the annuluses need not have equal widths. Each annulus A1-A4 can be independent of the others, meaning that its opacity can be controlled independently of the others. Independent control of the opacity of each annulus allows control over both the presence and size of the pinhole aperture, and allows a trade-off between light intensity and depth of field. Effectively, then, pinhole mask 400 provides a variable-size pinhole.

Figure 4A:
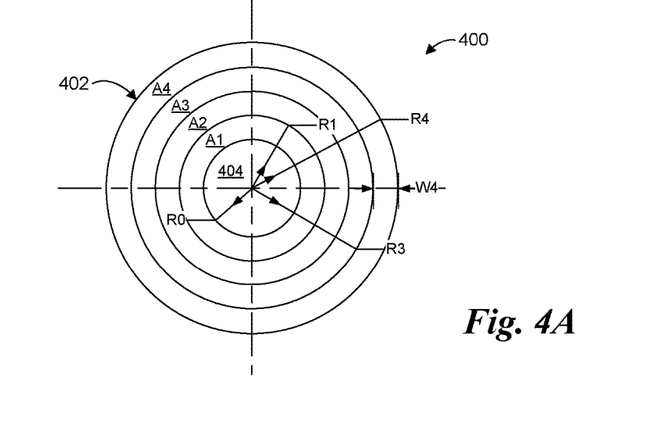
FIGS. 4A-4E are plan views of another embodiment of a pinhole mask.
Figure 4B:
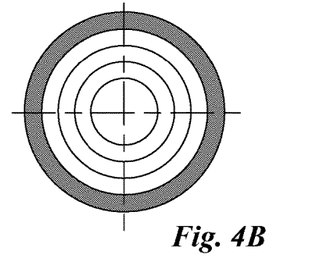
Figure 4C:
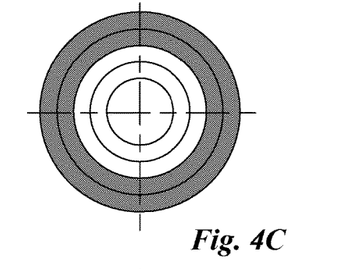
Figure 4D:
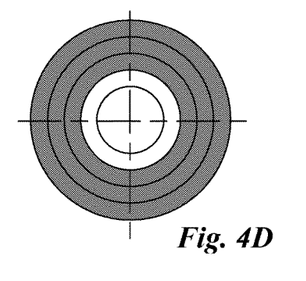
Figure 4E:
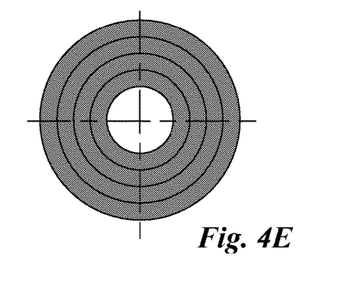

FIGS. 4B-4E illustrate an embodiment of operation of pinhole mask 400. Independent operation of annuluses A1-A4 allows control over the pinhole size by controlling the number of opaque annuluses and their individual opacities: the pinhole is largest when no annuluses are opaque and gets smaller as the number of opaque annuluses increases. In FIG. 4B, only outermost annulus A4 is opaque, leading to a pinhole with radius R3. In FIG. 4C, two annuluses A3-A4 are opaque, making the pinhole smaller with radius R2. In FIG. 4D three annuluses A2-A4 are made opaque, making the pinhole smaller still with radius R1. And finally, in FIG. 4E, four annuluses A1-A4 are opaque, so that the pinhole is formed by central aperture 404, which has the smallest available pinhole radius R0.

FIGS. 5A-5E illustrate another embodiment of a dynamic pinhole mask that can be used in an intraocular lens system such as intraocular lens 300. Pinhole mask 500 is in most respects similar to pinhole mask 400: it includes multiple concentric annuluses A1-A4, and a central area 504 that is not covered by any of annuluses A1-A4 and hence remains permanently transparent. As in pinhole mask 400, the illustrated embodiment of pinhole mask 500 includes four annuluses A1-A4, but other embodiments pinhole mask 500 can have a different number of annuluses, typically two or greater.

Figure 5A:
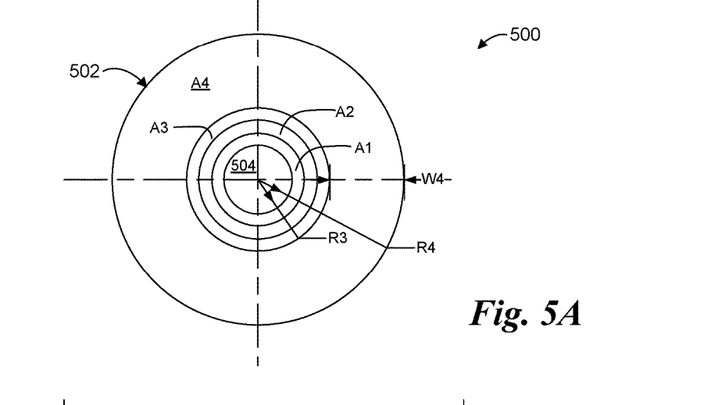
FIGS. 5A-5E are plan views of another embodiment of a pinhole mask.

The primary difference between pinhole mask 500 and pinhole mask 400 is that the annuluses in pinhole mask 500 do not all have the same width. Outermost annulus A4, for instance, has a large width W4, equal to R4−R3, while remaining annuluses A1-A3 have substantially smaller widths W1, W2, and W3. In the illustrated embodiment annuluses A1-A3 all have the same width (W1=W2=W3), but in other embodiments they need not all have the same width.

As before, each annulus A1-A4 can be independent of the others, meaning that its opacity can be controlled independently of the others. Independent control of the opacity of each annulus allows some control over the size of the pinhole aperture, and allows a trade-off between light intensity and focus. Effectively, then, pinhole mask 500 also provides a variable-size pinhole with fine control over the pinhole size.

FIGS. 5B-5E illustrate an embodiment of operation of pinhole mask 500. Pinhole mask 500 operates similarly to pinhole mask 400: independent operation of annuluses A1-A4 allows control over the size of the pinhole size by controlling the number of opaque annuluses and their individual opacities. But in pinhole mask 500 the distribution of annulus widths provides finer control of a small pinhole size.

Figure 5B:
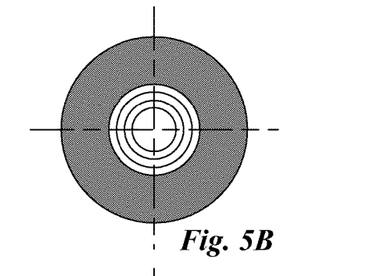
Figure 5C:
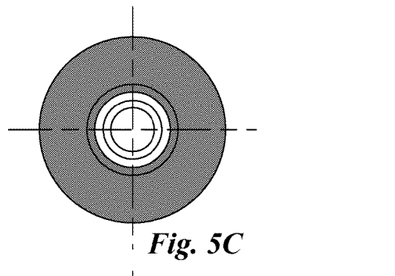
Figure 5D:
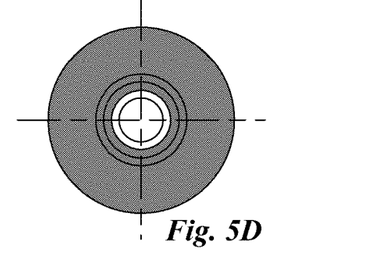
Figure 5E:
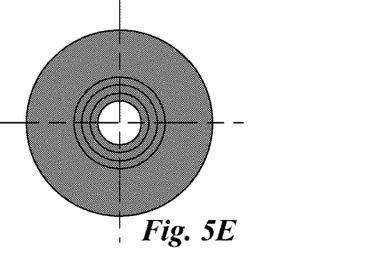

The pinhole is biggest when no annulus is opaque and gets smaller as the number of opaque annuluses increases. In FIG. 5B, only outermost annulus A4 is opaque, leading to an initial large drop in size of the optical aperture to a pinhole with radius R3. In FIG. 5C, annuluses A3-A4 are opaque, making the small pinhole even smaller with radius R2. In FIG. 5D annuluses A2-A4 are made opaque, making the pinhole smaller still with radius R1. And finally, in FIG. 5E, annuluses A1-A4 are all opaque, so that the pinhole is formed by central aperture 504, which has the smallest available pinhole radius R0.

Figure 6:
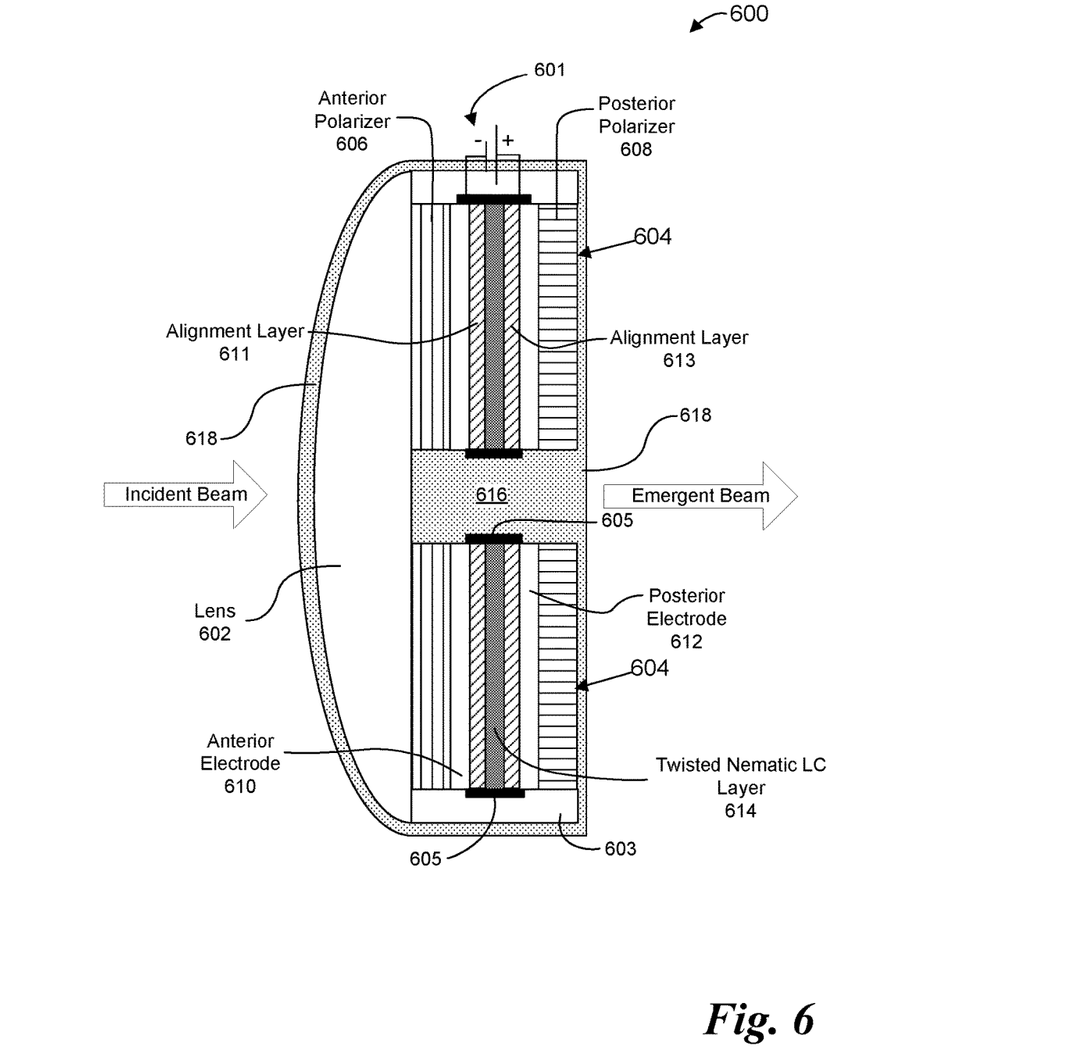
FIG. 6 is a cross-sectional view of an embodiment of a pinhole mask.

FIG. 6 illustrates a cross-section of an embodiment of an intraocular lens 600 with a dynamic pinhole mask. Intraocular lens 600 is one potential embodiment of intraocular lens 300; embodiments of intraocular lenses with pinhole masks 400 and 500 could have similar structures but the mask would be segmented into more annuluses than shown here and can include more or different electrode layers to accommodate the greater number of annuluses.

Intraocular lens 600 includes a lens 602 with a dynamic pinhole mask 604 and supporting electronics 603 formed on its surface. Lens 602 can have positive or negative optical power. In the illustrated embodiment lens 602 is a plano-convex lens, but in other embodiment it need not be plano-convex but can instead be plano-concave, bi-convex, bi-concave, or some other type of lens. And although lens 602 is illustrated as a single-element lens, in other embodiments it can be a compound lens with multiple elements. Lens 602 restores distance vision after the wearer's natural intraocular lens is removed.

Pinhole mask 604 is annular and includes an anterior polarizer 606 and a posterior polarizer 608. A liquid crystal assembly is sandwiched between polarizers 606 and 608. The liquid crystal assembly includes a liquid crystal layer 614 sandwiched between anterior alignment layer 611 and posterior alignment layer 613, as well as between anterior electrode 610 and posterior electrode 612. In the illustrated embodiment the liquid crystal layer 614 is a twisted nematic liquid crystal layer, but in other embodiments other types of polarizing liquid crystal materials can be used.

Anterior electrode 610 and posterior electrode 612 are electrically coupled to voltage source 601, which can be an alternating current (AC) source or a direct current (DC) source and can have a controllable voltage and current. In IOL 600, for instance, power supply 601 can correspond to power source 306 of IOL 300. Pinhole mask 604 operates using a direct current (DC) voltage or an alternating current (AC) voltage, typically less than 5 V and with a current draw that is typically a few microamps (µA).

One or both of alignment layers 611 and 613 can have a thickness of 10 nm to 10 microns, although embodiments are not limited to these thicknesses. Alignment layers 611 and 613 can comprise polyimide or other suitable material to provide for changing an alignment of liquid crystal molecules in LC layer 614. Although the illustrated embodiment of pinhole mask 604 has two alignment layers, anterior 611 and posterior 613, other embodiments could use one or none.

In an embodiment of pinhole mask 604 that includes a liquid or gel liquid crystal layer 614, it can be necessary to seal the inner and outer edges of mask 604 to prevent the liquid from escaping into the eye. In the illustrated embodiment the inner and outer edges of pinhole mask 604 are sealed with small dam structures 605, but in other embodiments they can be sealed in other ways—for instance, by crimping together excess electrode, alignment layer, and polarizer material at the edges. If used, dam structures 605 on the inner edges of mask 604 should be made of optically transparent materials, or at least materials that cause no large change in overall transparency, to ensure no optical artifacts are generated (glare, scatter, etc.).

The elements of IOL 600—lens 602, pinhole mask 604, electronics 603, etc.—are encapsulated within an optically transparent biocompatible encapsulation layer 618. Encapsulation layer 618 can be formed of any of the materials mentioned above in connection with FIG. 2. Encapsulation layer 618 fully encapsulates IOL 600 and fills the center section of pinhole mask 604 so that pinhole 616 is not a physical void or aperture in the back side of IOL 600.

In operation of IOL 600, when no voltage is applied to anterior electrode 610 and posterior electrode 612 so that no electric field is applied to pinhole mask 604, pinhole mask 604 is substantially transparent and incident light passes straight through the pinhole mask with little or no change in brightness. In other words, the emergent beam has substantially the same intensity as the incident beam. But when a voltage is applied across anterior electrode 610 and posterior electrode 612 the liquid crystals in liquid crystal layer 614 reorient themselves, changing the polarization of the light so that pinhole mask 604 becomes more opaque and forms pinhole 616. As a result, except for light traveling through pinhole 616 the emergent beam will have a lower intensity after passing through the mask (i.e., it will be dimmer) than the incident beam.

Figure 7:
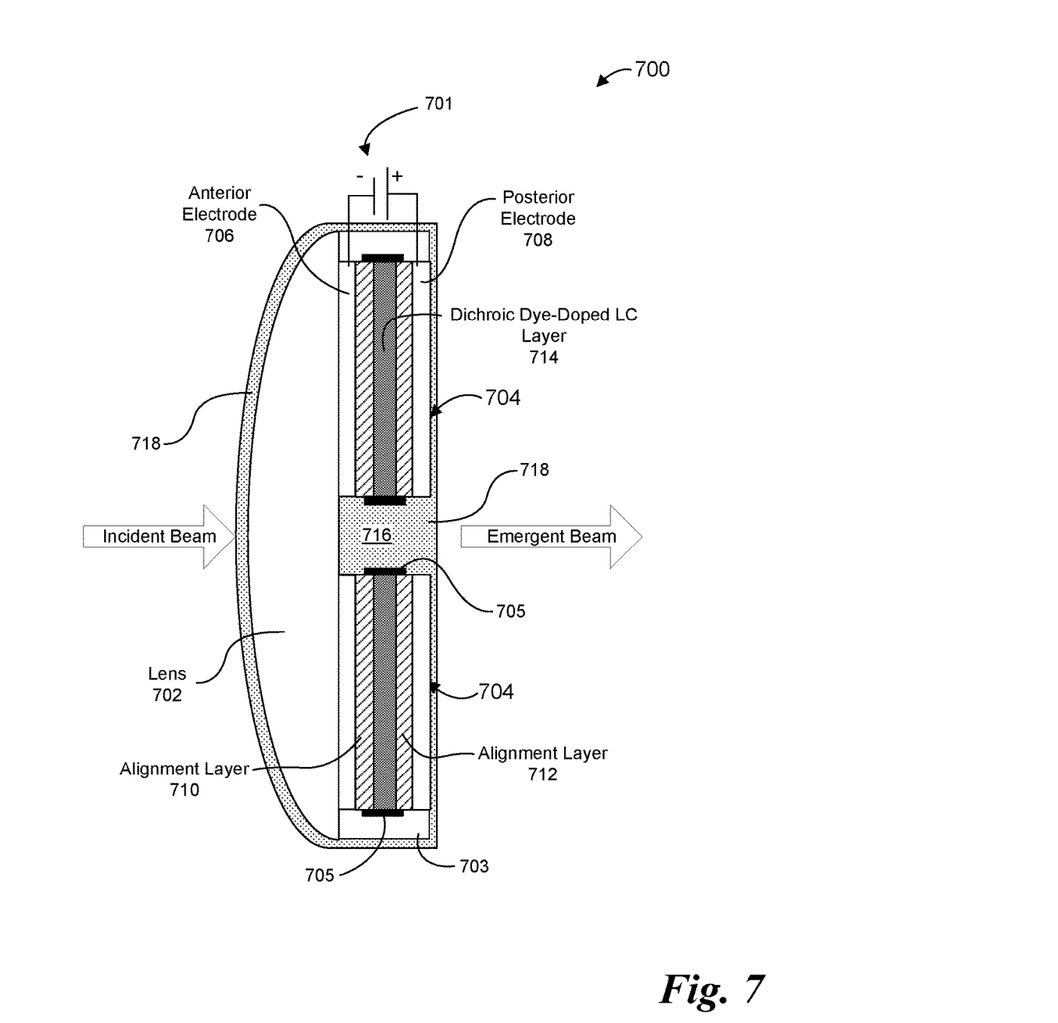
FIG. 7 is a cross-sectional view of another embodiment of a pinhole mask.

FIG. 7 illustrates a cross-sectional view of another embodiment of an intraocular lens 700. Intraocular lens 700 is one potential embodiment of intraocular lens 300; embodiments of intraocular lenses with pinhole masks 400 and 500 could have similar structures but the mask would be segmented into more annuluses than shown here and can include more or different electrode layers to accommodate the greater number of annuluses.

Intraocular lens 700 includes a lens 702 with a dynamic pinhole mask 704 and supporting electronics 703 formed on its surface. Lens 702 can have positive or negative optical power. In the illustrated embodiment lens 702 is a plano-convex lens, but in other embodiment it need not be plano-convex, but can instead be plano-concave, bi-convex, bi-concave, or some other type of lens. And although lens 702 is illustrated as a single-element lens, in other embodiments it can be a compound lens with multiple elements. Lens 702 restores distance vision after the wearer's natural intraocular lens is removed.

Pinhole mask 704 is annular and includes anterior electrode 706 and posterior electrode 708. Alignment layers 710 and 712 are sandwiched between electrodes 706 and 708, with anterior alignment layer 710 along the inner surface of anterior electrode 706 and posterior alignment layer 712 along the inner surface of posterior electrode 708. A dichroic dye-doped liquid crystal (LC) layer 714 is in turn sandwiched between alignment layers 710 and 712. Anterior electrode 706 and posterior electrode 708 are electrically coupled to voltage source 701, which can be an alternating current (AC) source or a direct current (DC) source and can have a controllable voltage and current. In IOL 700 power source 701 can correspond to power source 306 in IOL 300.

In one embodiment dichroic dye-doped LC layer 714 uses a dichroic dye-doped liquid crystal (LC). As a result, only a single layer of dynamic material (i.e., material that changes under the influence of an applied voltage) is required and no polarizing films are required. In one embodiment, layer 714 can comprise a nematic liquid crystal host with a negative dielectric anisotropy that is homeotropically (vertically) aligned. EC liquid crystal systems are made by doping a dichroic dye guest into a liquid crystal host. The dichroic dye S-428 (Mitsui Chemicals, Japan) is a suitable guest candidate as it has fairly uniform absorption over the visible spectrum and turns a normally colorless liquid crystal gray. Commercially available liquid crystalline materials can be used as the host, including, but not limited to: E7, BL111, MLC-2140, and MLC-2079, all available from Merck/EMD performance materials.

One or both of alignment layers 710 and 712 can have a thickness of 10 nm to 10 microns, although embodiments are not limited to these thicknesses. Alignment layers 710 and 712 can comprise polyimide or other suitable material to provide for changing an alignment of liquid crystal molecules in dichroic dye-doped LC layer 714. Although the illustrated embodiment of pinhole mask 704 has two alignment layers, anterior 710 and posterior 712, other embodiments could use one or none.

In an embodiment of pinhole mask 704 that includes a liquid or gel liquid crystal layer 714, it can be necessary to seal the inner and outer edges of mask 704 to prevent the liquid from escaping into the eye. In the illustrated embodiment the inner and outer edges of pinhole mask 704 are sealed with small dam structures 705, but in other embodiments they can be sealed in other ways—for instance, by crimping together excess electrode and alignment layer material at the edges. If used, dam structures 705 on the inner edge of mask 704 should be made of optically transparent materials, or at least materials that cause no large change in overall transparency, to ensure no optical artifacts are generated (glare, scatter, etc.).

The elements of IOL 700—lens 702, pinhole mask 704, electronics 703, etc.—are encapsulated within an optically transparent biocompatible encapsulation layer 718. Encapsulation layer 718 can be formed of any of the materials mentioned above in connection with FIG. 2. Encapsulation layer 718 fully encapsulates IOL 700 and fills the center section of pinhole mask 704 so that pinhole 716 is not a physical void or aperture in the back side of IOL 700.

In operation of pinhole mask 700, when no voltage is applied to anterior electrode 710 and posterior electrode 712—meaning that no voltage or current is applied to dichroic dye-doped LC layer 714—both the LC molecules and the dye molecules are aligned perpendicular to the surface of the lens and the wearer will be looking down the long axis of the dye molecules where the optical absorption will be at its minimum value. Incident light thus passes straight through pinhole mask 704 substantially without change to its brightness; in other words, the emergent beam has substantially the same intensity as the incident beam.

But when an AC voltage waveform is applied to electrodes 710 and 712, the LC molecules will rotate and carry the dye molecules along with them. As the magnitude of the applied voltage increases so too will the rotation angle of the LC and dye molecules, until they are approximately parallel to the surface of the lens. In this orientation opacity of pinhole mask 704 will be at a maximum and pinhole 716 is formed. As a result, except for light traveling through pinhole 716 the emergent beam will have a lower intensity (i.e., it will be dimmer) after passing through the mask than the incident beam. Such liquid crystal-based pinhole masks operate with AC voltage waveforms with amplitudes between 2 and 10 volts (4-20 Vp-p) at frequencies above 50 Hz. Current draw is typically in the nano-amp (nA) to micro-amp (μA) range so they have very low power consumption.

Figure 8:
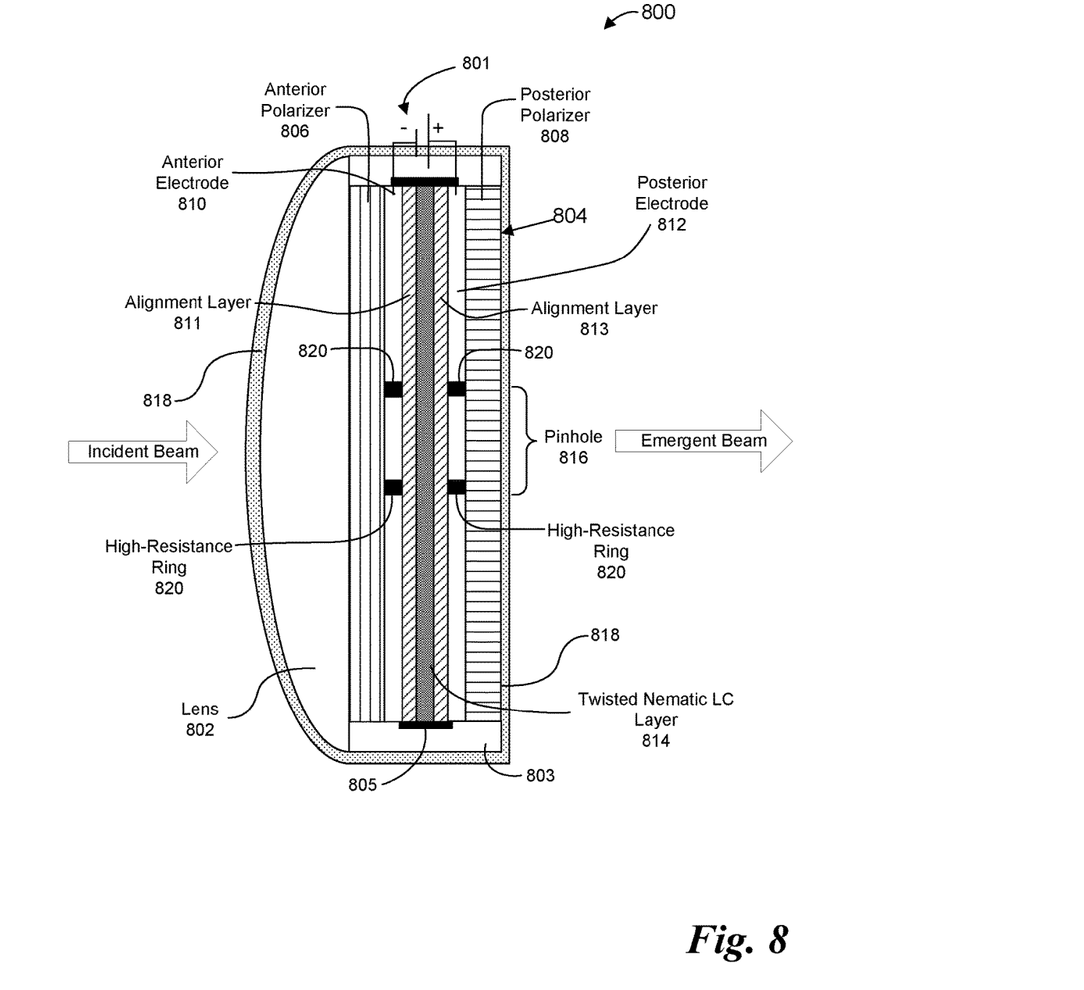
FIG. 8 is a cross-sectional view of another embodiment of a pinhole mask.

FIG. 8 illustrates a cross-section of an embodiment of an intraocular lens 800 with a dynamic pinhole mask. Intraocular lens 800 is a potential embodiment of intraocular lens 300; embodiments of intraocular lenses with pinhole masks 400 and 500 could have similar structures but the mask would be segmented differently than shown. Intraocular lens 800 is in most respects similar to IOL 600 and different embodiments can have all the same variations as IOL 600. The primary difference between IOL 800 and IOL 600 is that in IOL 800 pinhole mask 804 is circular rather than annular, meaning that the mask covers all or most of the lens surface on which it is formed.

The construction of mask 804 is similar to the construction of mask 604 and the mask and all its elements can have the same variations. Pinhole mask 804 is formed on lens 802 and includes an anterior polarizer 806 and a posterior polarizer 808 and a liquid crystal assembly is sandwiched between polarizers 806 and 808. The liquid crystal assembly includes a liquid crystal layer 814 sandwiched between alignment layers 811 and 813 as well as between anterior electrode 810 and posterior electrode 812.

Anterior electrode 810 and posterior electrode 812 are electrically coupled to voltage source 801, which can be an alternating current (AC) source or a direct current (DC) source and can have a controllable voltage and current. In IOL 800, for instance, power supply 801 can correspond to power source 306 of IOL 300. Pinhole mask 804 operates using a direct current (DC) voltage or an alternating current (AC) voltage, typically less than 5 V and with a current draw that is typically a few microamps (μA). To allow a central portion of mask 804 to remain clear (i.e., higher transmission or low capacity) while the rest of the mask becomes opaque, high-resistance rings 820 can be formed in the anterior and posterior electrodes. High-resistance rings 820 can be filled with a high-resistance material in one embodiment, but in other embodiments high-resistance rings 820 can simply be unfilled gaps in the electrodes. If rings 820 are filled with a material it should be an optically transparent material, or at least a material that causes no large change in overall transparency, to ensure no optical artifacts are generated (glare, scatter, etc.). However built, high-resistance rings 820 prevent current from reaching the central part of electrodes 810 and 812, so that the central part of mask 804 that is within the high-resistance rings will not change its opacity when current is applied and will form pinhole 816.

As in IOL 600, in IOL 800 it can be necessary to seal the edge of mask 804 to prevent liquid from escaping into the eye. In the illustrated embodiment the outer edge of pinhole mask 804 is sealed with a small dam structure 805, but in other embodiments it can be sealed differently—for instance by crimping together excess electrode, alignment layer, and polarizer material at the edges. Also as in IOL 600, the elements of IOL 800 are encapsulated within an optically transparent biocompatible encapsulation layer 818. Encapsulation layer 818 can be formed of any of the materials mentioned above in connection with FIG. 2.

In operation of IOL 800, when no voltage is applied to anterior electrode 810 and posterior electrode 812 so that no electric field is applied to pinhole mask 804, pinhole mask 804 is substantially transparent and incident light passes straight through the pinhole mask with little or no change to its brightness. In other words, the emergent beam has substantially the same intensity as the incident beam. But when a voltage is applied across anterior electrode 810 and posterior electrode 812 the liquid crystals in the parts of layer 814 outside high-resistance rings 820 reorient themselves, changing the polarization of the light so that the part of pinhole mask 804 outside high-resistance rings 820 becomes more opaque and forms pinhole 816. As a result, except for light traveling through pinhole 816 the emergent beam will have a lower intensity after passing through the mask (i.e., it will be dimmer) than the incident beam.

Figure 9:
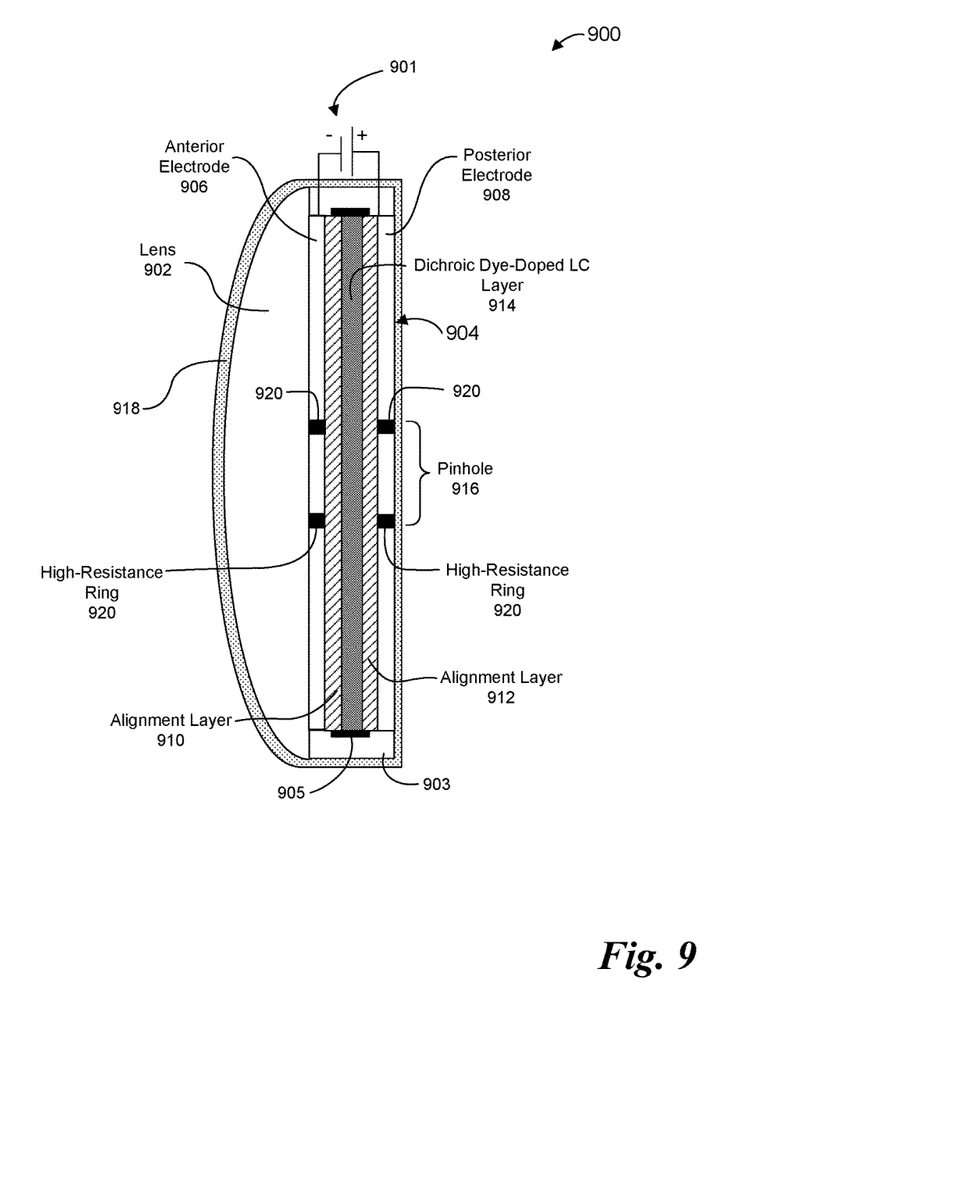
FIG. 9 is a cross-sectional view of another embodiment of a pinhole mask.

FIG. 9 illustrates a cross-sectional view of another embodiment of an intraocular lens 900. Intraocular lens 900 is one potential embodiment of intraocular lens 300; embodiments of intraocular lenses with pinhole masks 400 and 500 could have similar structures but the mask would be segmented differently than shown. Intraocular lens 900 is in most respects similar to IOL 700 and different embodiments can have all the same variations as IOL 700. The primary difference between IOL 900 and IOL 700 is that in IOL 900 pinhole mask 904 is circular rather than annular, meaning that the mask covers all or most of the lens surface on which it is formed.

The construction of mask 904 is similar to the construction of mask 704 and the mask and all its elements can have the same variations. Pinhole mask 904 is formed on lens 902 and includes anterior electrode 906 and posterior electrode 908. Alignment layers 910 and 912 are sandwiched between electrodes 906 and 908, with anterior alignment layer 910 along the inner surface of anterior electrode 906 and posterior alignment layer 912 along the inner surface of posterior electrode 908. A dichroic dye-doped liquid crystal (LC) layer 914 is in turn sandwiched between alignment layers 910 and 912. Anterior electrode 906 and posterior electrode 908 are electrically coupled to voltage source 901, which can be an alternating current (AC) source or a direct current (DC) source and can have a controllable voltage and current. In IOL 900 power source 901 can correspond to power source 306 in IOL 300.

In an embodiment of pinhole mask 904 that includes a liquid or gel liquid crystal layer 914, it can be necessary to seal the outer edge of mask 904 to prevent liquid from escaping into the eye. In the illustrated embodiment the outer edge of pinhole mask 904 is sealed with small dam structure 905, but in other embodiments it can be sealed differently—for instance, by crimping together excess electrode and alignment layer material at the edge. The elements of IOL 900 are also encapsulated within an optically transparent biocompatible encapsulation layer 918, which can be formed of any of the materials mentioned above in connection with FIG. 2.

To allow a central portion of mask 904 to remain clear (i.e., higher transmission or low capacity) while the rest of the mask becomes opaque, high resistance rings 920 can be formed in the anterior and posterior electrodes. High-resistance rings 920 can be filled with a high-resistance material in one embodiment, but in other embodiments high-resistance rings 920 can simply be unfilled gaps in the electrodes. If rings 920 are filled with a material it should be an optically transparent material, or at least a material that causes no large change in overall transparency, to ensure no optical artifacts are generated (glare, scatter, etc.). However built, high-resistance rings 920 prevent current from reaching the central part of electrodes 906 and 908, so that the central part of mask 904 that is within the high-resistance rings will not change its opacity when current is applied and the mask will form pinhole 916.

In operation of pinhole mask 900, when no voltage is applied to anterior electrode 910 and posterior electrode 912—meaning that no voltage or current is applied to dichroic dye-doped LC layer 914—both the LC molecules and the dye molecules are aligned perpendicular to the surface of the lens and the wearer will be looking down the long axis of the dye molecules where the optical absorption will be at its minimum value. Incident light thus passes straight through pinhole mask 904 substantially without change to its brightness; in other words, the emergent beam has substantially the same intensity as the incident beam.

When an AC voltage waveform is applied to electrodes 910 and 912, in the parts of layer 914 outside high-resistance rings 920 the LC molecules will rotate and carry the dye molecules along with them. As the magnitude of the applied voltage increases so too will the rotation angle of the LC and dye molecules, until they are approximately parallel to the surface of the lens. In this orientation opacity of the part of pinhole mask 904 outside high-resistance rings 920 will be at a maximum and pinhole 916 is formed. As a result, except for light traveling through pinhole 916 the emergent beam will have a lower intensity (i.e., it will be dimmer) after passing through the mask than the incident beam. Such liquid crystal-based pinhole masks operate with AC voltage waveforms with amplitudes between 2 and 10 volts (4-20 Vp-p) at frequencies above 50 Hz. Current draw is typically in the nano-amp (nA) to micro-amp (µA) range so they have very low power consumption.

The above description of embodiments, including what is described in the abstract, is not intended to be exhaustive or to limit the invention to the described forms. Specific embodiments of, and examples for, the invention are described herein for illustrative purposes, but various equivalent modifications are possible within the scope of the invention in light of the above detailed description, as those skilled in the relevant art will recognize.

The terms used in the following claims should not be interpreted to limit the invention to the specific embodiments disclosed in the specification and the claims. Rather, the scope of the invention is to be determined entirely by the following claims, which are to be interpreted using established claim interpretation doctrines.

The invention claimed is:

1. An intraocular lens comprising:
   a lens having a center and having positive or negative optical power; and
   a pinhole mask formed on the lens, the pinhole mask comprising:
      one or more annular sections concentrically aligned, each of the one or more annular sections having variable opacity, each of the one or more annular sections including a liquid crystal layer having an annular shape that encircles a central hole through the liquid crystal layer; and
      a central section that is permanently transparent, a radius of the central section being adapted to allow the central section to act as a pinhole when the one or more annular sections are made opaque, wherein the central hole in the liquid crystal layer of each of the one or more annular sections encircles the central section.

2. The intraocular lens of claim 1 wherein the one or more annular sections comprise a single annular section.

3. The intraocular lens of claim 1 wherein the one or more annular sections comprise a plurality of concentric annuluses.

4. The intraocular lens of claim 3 wherein the one or more annular sections comprise plurality of concentric annuluses of equal width.

5. The intraocular lens of claim 3 wherein the one or more annular sections comprise a plurality of concentric annuluses each having a width, wherein the width of an outermost annular section is greater than the width of any annular section closer to the center of the lens.

6. The intraocular lens of claim 1 wherein the pinhole mask further comprises:
an anterior electrode and a posterior electrode, the anterior electrode disposed on a surface of the len,
wherein the liquid crystal layer is sandwiched between the anterior electrode and the posterior electrode, the liquid crystal layer including a liquid crystal material with a guest dye.

7. The intraocular lens of claim 6 wherein the guest dye is a dichroic dye.

8. The intraocular lens of claim 6 wherein the pinhole mask further comprises one or both of:
an anterior alignment layer between the anterior electrode and the liquid crystal material, and
a posterior alignment layer between the posterior electrode and the liquid crystal material.

9. The intraocular lens of claim 6 wherein the pinhole mask is operated with an alternating current (AC) voltage waveform of amplitude substantially between 2 volts and 10 volts.

10. The intraocular lens of claim 9 wherein the AC voltage waveform has a frequency equal to or greater than 50 Hz.

11. The intraocular lens of claim 1 wherein the pinhole mask comprises:
anterior and posterior polarizers, the anterior polarizer positioned at a different angular orientation than the posterior polarizer,
wherein the liquid crystal layer is sandwiched between the anterior and posterior polarizers, the liquid crystal layer comprising an anterior electrode, a posterior electrode, and a layer of twisted nematic liquid crystal sandwiched between the anterior electrode and the posterior electrode.

12. An intraocular lens system comprising:
a lens having a center and having positive or negative optical power;
a pinhole mask formed on the lens, the pinhole mask comprising:
one or more annular sections concentrically aligned, each of the one or more annular sections having variable opacity, each of the one or more annular sections including a liquid crystal layer having an annular shape that encircles a central hole through the liquid crystal layer; and
a central section that is permanently transparent, a radius of the central section being adapted to allow the central section to act as a pinhole when the one or more annular sections are made opaque, wherein the central hole in the liquid crystal layer of each of the one or more annular sections encircles the central section;
one or more sensors positioned on the lens; and
a controller disposed on a peripheral part of the lens and electrically coupled to the one or more sensors and to the pinhole mask.

13. The intraocular lens system of claim 12 wherein the one or more annular sections comprise a single annular section.

14. The intraocular lens system of claim 12 wherein the one or more annular sections comprise a plurality of concentric annuluses.

15. The intraocular lens system of claim 14 wherein the one or more annular sections comprises a plurality of concentric annuluses of equal width.

16. The intraocular lens system of claim 14 wherein the one or more annular sections comprise a plurality of concentric annuluses each having a width, wherein the width of an outermost annular section is greater than the width of any annular section closer to the center of the lens.

17. The intraocular lens system of claim 13 wherein the pinhole mask comprises:
an anterior electrode and a posterior electrode, the anterior electrode disposed on a surface of the lens,
wherein the liquid crystal layer is sandwiched between the anterior electrode and the posterior electrode, the liquid crystal layer including a liquid crystal material with a guest dye.

18. The intraocular lens system of claim 17 wherein the guest dye is a dichroic dye.

19. The intraocular lens system of claim 17 wherein the pinhole mask further comprises one or both of:
an anterior alignment layer between the anterior electrode and the liquid crystal material, and
a posterior alignment layer between the posterior electrode and the liquid crystal material.

20. The intraocular lens system of claim 17 wherein the pinhole mask is operated with an alternating current (AC) voltage waveform of amplitude substantially between 2 volts and 10 volts.

21. The intraocular lens system of claim 20 wherein the AC voltage waveform has a frequency equal to or greater than 50 Hz.

22. The intraocular lens system of claim 12 wherein the pinhole mask comprises:
anterior and posterior polarizers, the anterior polarizer positioned at a different angular orientation than the posterior polarizer,
wherein the liquid crystal layer is sandwiched between the anterior and posterior polarizers, the liquid crystal layer comprising an anterior electrode, a posterior electrode, and a layer of twisted nematic liquid crystal sandwiched between the anterior electrode and the posterior electrode.

23. The intraocular lens system of claim 12 wherein the controller can use the output of the one or more sensors to determine whether a wearer is attempting to use near vision and activate the pinhole mask in response to a near-vision determination.

24. The intraocular lens system of claim 23 wherein the one or more sensors include strain gauges, electrical sensors, or optical sensors.

25. The intraocular lens of claim 11, wherein the anterior and posterior polarizers have annular shapes and encircle the central section.

26. The intraocular lens of claim 1, further comprising:
an encapsulation layer that encapsulates the lens and pinhole mask and extends into the central section of the pinhole mask and fills into the central hole through the liquid crystal layer.

27. The intraocular lens of claim 26, wherein the encapsulation layer is fabricated of an optically transparent, biocompatible material.

28. The intraocular lens of claim 1, further comprising:
- a sensor system configured to sense whether a user is attempting to use a near vision or a distance vision, the sensor system disposed peripherally to the pin hole mask within the intraocular lens; and
- a controller coupled to the sensor system and the pinhole mask, the controller including logic to activate the pinhole mask in response to a determination, based upon feedback from the sensor system, that the user is attempting to use the near vision.

* * * * *